US010350032B2

(12) United States Patent
Jahns et al.

(10) Patent No.: US 10,350,032 B2
(45) Date of Patent: Jul. 16, 2019

(54) PROCESS FOR SELECTIVELY TREATING THE SURFACE OF DENTAL CERAMIC

(71) Applicant: 3M INNOVATIVE PROPERTIES COMPANY, St. Paul, MN (US)

(72) Inventors: Michael Jahns, Gilching (DE); Jacqueline C. Rolf, River Falls, WI (US); Dajana Zimmermann, Amersee (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 15/128,637

(22) PCT Filed: Mar. 18, 2015

(86) PCT No.: PCT/US2015/021247
§ 371 (c)(1),
(2) Date: Sep. 23, 2016

(87) PCT Pub. No.: WO2015/148215
PCT Pub. Date: Oct. 1, 2015

(65) Prior Publication Data
US 2017/0105818 A1 Apr. 20, 2017

(30) Foreign Application Priority Data
Mar. 25, 2014 (EP) ..................................... 14161480

(51) Int. Cl.
*A61C 8/00* (2006.01)
*A61K 6/02* (2006.01)
(Continued)

(52) U.S. Cl.
CPC .............. *A61C 8/0015* (2013.01); *A61C 5/77* (2017.02); *A61C 7/00* (2013.01); *A61C 8/0048* (2013.01);
(Continued)

(58) Field of Classification Search
CPC ....... A61C 8/0015; A61C 8/48; A61C 13/082; A61C 13/0006; A61C 13/081; A61C 7/00;
(Continued)

(56) References Cited

U.S. PATENT DOCUMENTS 6,105,761 A 8/2000 Peuker
6,709,694 B1 3/2004 Suttor
(Continued)

FOREIGN PATENT DOCUMENTS

WO WO 2000-046168 8/2000
WO WO 2004-110959 12/2004
(Continued)

OTHER PUBLICATIONS

International Search Report for PCT International Application No. PCT/US2015/021247, dated Jun. 23, 2015, 4 pages.

*Primary Examiner* — Matthew M Nelson (57) ABSTRACT

The invention relates to a process for selectively treating parts of the surface of a porous dental zirconia article, the process comprising the steps of providing a liquid composition and a porous 3-dimensional dental zirconia article having an outer and inner surface, applying the liquid composition to only a part the outer surface and/or inner surface of the porous dental zirconia article, the liquid composition comprising a whitening agent comprising a phosphorous containing component, the phosphorous containing component comprising a phosphate, phosphone or phosphine moiety, with the proviso that at least one P—O unit of the phosphate, phosphone or phosphine moiety is dissociable or able to otherwise interact with zirconia. The invention also relates to a dental zirconia article obtainable or obtained by such a process and a kit of parts comprising a container containing a certain liquid composition.

12 Claims, 1 Drawing Sheet

(51) Int. Cl.
  *C04B 41/85* (2006.01)
  *C04B 41/00* (2006.01)
  *C04B 41/50* (2006.01)
  *A61C 5/77* (2017.01)
  *A61C 7/00* (2006.01)
  *A61C 13/00* (2006.01)
  *A61C 13/08* (2006.01)
  *A61C 19/06* (2006.01)
  *B05D 1/28* (2006.01)
  *B05D 3/10* (2006.01)
  *B05D 3/12* (2006.01)
  *C04B 111/00* (2006.01)
  *C04B 111/80* (2006.01)

(52) U.S. Cl.
  CPC ........ *A61C 13/0006* (2013.01); *A61C 13/081* (2013.01); *A61C 13/082* (2013.01); *A61C 19/066* (2013.01); *A61K 6/024* (2013.01); *A61K 6/0205* (2013.01); *B05D 1/28* (2013.01); *B05D 3/108* (2013.01); *B05D 3/12* (2013.01); *C04B 41/009* (2013.01); *C04B 41/5092* (2013.01); *C04B 41/85* (2013.01); *C04B 2111/00836* (2013.01); *C04B 2111/80* (2013.01)

(58) Field of Classification Search
  CPC ........ A61C 19/066; A61C 5/77; A61K 6/024; B05D 3/108; B05D 3/12; B05D 1/28

USPC .................................................. 433/203.1
  See application file for complete search history.

(56) References Cited

U.S. PATENT DOCUMENTS

| | | | |
|---|---|---|---|
| 7,097,075 B2 | 8/2006 | Peuker | |
| 9,095,403 B2* | 8/2015 | Carden | A61K 6/0005 |
| 2004/0258723 A1* | 12/2004 | Singh | A61C 19/063 424/401 |
| 2005/0084823 A1* | 4/2005 | Foser | A61C 13/09 433/202.1 |
| 2006/0117989 A1 | 6/2006 | Hauptmann | |
| 2008/0070191 A1* | 3/2008 | Ricks | A61C 13/083 433/202.1 |
| 2008/0274066 A1* | 11/2008 | Montgomery | A61C 19/06 424/53 |
| 2012/0237579 A1* | 9/2012 | Singh | A61C 19/066 424/401 |

FOREIGN PATENT DOCUMENTS

| | | |
|---|---|---|
| WO | WO 2008-098157 | 8/2008 |
| WO | WO 2009-014903 | 1/2009 |
| WO | WO 2013-022612 | 2/2013 |
| WO | WO 2013-055432 | 4/2013 |
| WO | WO 2013-070451 | 5/2013 |
| WO | WO 2014-093329 | 6/2014 |

* cited by examiner

PROCESS FOR SELECTIVELY TREATING THE SURFACE OF DENTAL CERAMIC

FIELD OF THE INVENTION

The invention relates to a process for selectively treating parts of the surface of a porous dental zirconia article. The invention also relates to a liquid composition which can be used in such a process, wherein the composition comprises a liquid and a whitening agent.

BACKGROUND ART

A dental ceramic can be coloured or opacified e.g. by incorporating pigments into the ceramic material from the very beginning or using metal salts containing solutions which are applied on the surface of a porous dental ceramic article with the aim to colour the dental ceramic article in its entirety. Colouring solutions are described in a couple of documents:

WO 00/46168 (corresponding to U.S. Pat. No. 6,709,694) refers to colouring ceramics by way of ionic or complex-containing solutions containing defined concentrations of at least one salts or complexes of the rare earth elements or of the elements of the subgroups. The solution might contain additives like stabilizers, complex builders, pigments and beating additives.

WO 2004/110959 (3M IPC) relates to a colouring solution for ceramic framework. The solution comprises a solvent (e.g. water), a metal salt and polyethylene glycol having a Mn in the range of 1.000 to 200.000.

WO 2008/098157 (3M IPC) relates to a colouring solution for dental ceramic framework comprising a solvent, a colouring agent comprising metal ions, and a complexing agent, wherein the amount of complexing agent is sufficient to dissolve the colouring agent in the solvent.

WO 2009/014903 (3M IPC) relates to a colouring solution for dental ceramic articles, the solution comprising a solvent and a colouring agent comprising rare earth element ions being present in the solution in an amount of at least 0.05 mol/l solvent and transition ions being present in the solution in an amount of 0.00001 to 0.05 mol/l solvent.

WO 2013/055432 (3M IPC) relates to aerogels, calcined and crystalline articles and methods of making the same are described. The content of this application is herewith incorporated by reference.

WO 2013/022612 (3M IPC) relates to colouring solutions for selectively treating the surface of dental ceramic articles. The solution comprises a solvent being miscible with water but not being water, an effect agent and a complexing agent.

Whitening agents are typically used to cover the metallic surface of a metallic dental framework in order to give the final dental restoration a more natural appearance. In certain cases, it can, however, also be desirable to opacify e.g. the inner surface of a ceramic framework to cover discolourations of the tooth stump.

In this respect WO 2013/070451 (3M IPC) describes a process for selectively treating parts of the surface of a porous dental ceramic using a composition comprising a liquid being miscible with water, but not being water, a whitening agent comprising nano-sized metal oxide particles, metal ion containing components or mixtures thereof which precipitate if the composition is adjusted to a pH above 5.

The present invention is intended to improve the known colouring and/or whitening processes.

SUMMARY OF THE INVENTION

In particular, it would be desirable to have a liquid composition, which can be used to selectively treat specific parts of the surface of porous dental ceramic in a simple and inexpensive way.

Moreover, it would be desirable if this can be done without a complete diffusion of the composition into the pores of pre-sintered or porous dental ceramic, so that a defined application of the composition can be accomplished.

At least one of these objects can be achieve by providing a process of selectively treating parts of the surface of a porous dental ceramic comprising the steps of
a) providing a liquid composition and a porous 3-dimensional dental zirconia article having an outer and inner surface,
b) applying the liquid composition to only a part the outer and/or inner surface of the porous dental zirconia article,
c) optionally drying the porous dental ceramic, and
d) optionally firing the porous dental ceramic,
the liquid composition comprising
    a whitening agent comprising a phosphorous containing component,
    the phosphorous containing component comprising a phosphate (PO4), phosphone (PO3) or phosphine moiety (PO2),
with the proviso that at least one P—O unit of the phosphate, phosphone or phosphine moiety is dissociable or able to bind to the zirconia surface of the dental zirconia article (e.g. by forming a complex) leading to a localized opacifying effect once the zirconia article is sintered.

The invention is also related to a kit of parts comprising
    the a receptacle containing the liquid composition described in the present text,
    a dental zirconia mill blank useful for producing a porous dental zirconia article as described the present text,
    optionally an instruction of use,
    optionally a receptacle containing a colouring liquid, and
    optionally an application device.

A further aspect of the invention is directed to the use of the liquid composition as described in the present text for selectively treating parts of the surface of a porous dental zirconia restoration.

In another aspect, the invention relates to a dental ceramic treated with the composition or obtainable by the process described in the present text.

Yet a further aspect of the invention is directed to a device comprising
    at least one compartment (A) containing the liquid composition as described in the present text;
    at least one compartment (B) containing a colouring liquid as described in the present text; and
    an instruction of use for conducting the process as described in the present text.
compartment (A) and compartment (B) being separated from each other by a pre-defined break zone.

Unless defined otherwise, for this description the following terms shall have the given meaning:

The term "dental article" is to be understood as an article which can and is to be used in the dental field. In this respect, the dental article shall have sufficient strength. Examples include inlays, onlays, veneers, crowns, abutments, bridges (including 2 parts, 3 parts, 4 parts, 5 parts or 6 parts bridges) and frameworks forming the support structure for a crown or bridge.

The dental article has usually a 3-dimensional inner and outer surface including convex and concave structures. Compared to other articles such as pottery or paving stones, the dental article is small and filigree. The thickness of the dental article can vary from very thin, e.g. at the edges and rims (below 0.1 mm) to considerably thick, e.g. in the biting area (up to 7 mm). Typically, the dental article described in the present text comprises or essentially consists after sintering of a polycrystalline ceramic material comprising Yttrium stabilized $ZrO_2$.

Examples of dental articles include crowns (including monolithic crowns), bridges, inlays, onlays, veneers, facings, copings, crown and bridged framework, implants, abutments, orthodontic appliances (e.g. brackets, buccal tubes, cleats and buttons) and parts thereof. The surface of a tooth is considered not to be a dental article.

A dental article should not contain components which are detrimental to the patient's health and thus free of hazardous and toxic components being able to migrate out of the dental article.

"Zirconia ceramic article" shall mean a 3-dimensional article wherein at least one the x, y, z dimension is at least 5 mm, the article being comprised of at least 80 wt.-% or at least 90 wt.-% zirconia.

"Ceramic" means an inorganic non-metallic material that is produced by application of heat. Ceramics are usually hard, porous and brittle and, in contrast to glasses or glass ceramics, display an essentially purely crystalline structure.

"Monolithic dental restoration" shall mean a dental article onto the surface of which no facing or veneer has been attached. That is, the monolithic dental restoration is essentially comprised out of only one material composition. However, if desired a thin glazing layer can be applied.

A "liquid composition" is any substance which is able to solubilise, dissolve or disperse the whitening agent. The liquid should be sufficiently chemically stable if combined with the whitening agent. That is, the liquid shall not be decomposed by the other components present in the composition. Depending on the chemical nature of the whitening agent, the liquid composition and the white agent can be identical.

A "whitening agent" is an agent, which is able to whiten the surface of a dental article either right after treatment of the article with the whitening agent or after conducting a firing step of the treated article. The whitening effect typically goes along with an increase in opacity.

"Soluble" means that a component (solid) can be completely dissolved within a solvent. That is, the substance is able to form individual molecules (like glucose) or ions (like sodium chloride) or non-settling particles (like a sol) when dispersed in water at 23° C. The solution process, however, might take some time, e.g. stirring the composition over a couple of hours (e.g. 10 or 20 h) might be required.

More specifically, according to the invention a substance or composition is defined as "soluble", if less than 10 wt.-% or less than 5 wt.-% or less than 2 wt.-% or less than 1 wt.-% or less than 0.1 wt.-% (with respect to the whole composition) of solid substance remains after the following procedure:

a. 800 mg of substance and 8.0 g of solvent are placed into a centrifuge test tube of known weight.
b. The test tube is closed and shaken for 60 minutes.
c. The mixture is centrifuged with centrifugal acceleration (ac) of 9870 m/s² for 20 min.
d. The supernatant liquid is decanted.
e. The precipitate is re-suspended with 6 g solvent.
f. The test tube is shaken for 60 min, centrifuged as described above, and the supernatant liquid decanted again.
g. Steps e) and f) are repeated one time.
h. The remaining precipitate is calcined for 12 h at 500° C. (+/−3.5° C.).
i. After cooling to room temperature the dry weight of the sample is determined and used for calculating the soluble fraction.

A substance or composition is defined as "insoluble", if more than 90 wt.-% or more than 50 wt.-% or more than 25 wt.-% or more than 10 wt.-% (with respect to the whole composition) of substance remains unsolved after the procedure described above.

The term "water-miscible" or "miscible with water" means that a certain liquid is miscible with water at 23° C. at least to a high extend to provide a homogeneous solution, i.e. without phase separation. More specifically, the water-miscible liquid is defined as miscible with water if at least 10 g or at least 100 g or at least 500 g or at least 750 g or least 1000 g water-miscible liquid is soluble in 1000 g water without phase separation. Ideally, no phase separation occurs at ambient conditions independent from the mixing ratio (e.g. ethanol is miscible with water in all ratios).

The term "amount sufficient to dissolve" describes the amount of an agent needed to fully dissolve a certain substance in a certain solvent so that a storage stable composition can be obtained. The time needed to dissolve a substance is not particularly limited, however, the dissolution should occur within a reasonable time (e.g. within 10 to 48 h) using common equipment like mechanical stirrers and heaters.

A component being described as being "dissociable" means that the component contains at least one moiety being able to generate ionic compounds e.g. like a salt or acid if dissolved in water.

A solution can be classified as "storage stable", if it remains stable over a considerable long period of time (at least 4 weeks to more than 12 months under ambient conditions). A storage stable solution typically does not show any visible (visible to the human eye) precipitation of the colouring agent during storage at ambient conditions (23° C., 1013 mbar) and does not show decomposition of the solution or precipitation of single or multiple components.

A "complex", also known as coordination compound, in chemistry usually is used to describe molecules or ensembles formed by the combination of ligands and metal ions. Originally, a complex implied a reversible association of molecules, atoms, or ions through weak chemical bonds. As applied to coordination chemistry, this meaning has evolved. Some metal complexes are formed virtually irreversibly and many are bound together by bonds that are quite strong. The ions or molecules surrounding the metal are called ligands. Ligands are generally bound to a metal ion by a coordinative bonding (donating electrons from a lone electron pair to the Lewis acidic metal center), and are thus said to be coordinated to the ion. Those ligands are referred to as "coordinating ligands".

"Localized opacifying effect" means that the opacifying effect is only visible after sintering (to the human eye) in those areas to which the liquid composition has been applied. "Rare earth elements" and/or of the subgroups of the rare earth elements include Ce, Pr, Nd, Sm, Eu, Gd, Tb, Dy, Ho, Er, Tm, Yb and Lu.

"Transition metals" comprise the metals listed in the columns of the Periodic Table of Elements starting with the elements Sc, Ti, V, Cr, Mn, Fe, Co, Ni, Cu and Zn and the metals listed below those elements.

Metals of the main groups comprise the metals listed in the main groups of the Periodic Table of Elements starting with the elements Li, Be, B, C, N, O, F and the metals listed below those elements.

A dental ceramic or dental article is classified as "pre-sintered" if the dental ceramic has been treated with heat (temperature range from 900 to 1100° C.) for 1 to 3 h to such an extent that the raw breaking resistance of the dental ceramic measured according to the "punch on three ball test" ISO 6872 is within a range of 15 to 55 MPa or 30 to 50 MPa. A pre-sintered dental ceramic usually has a porous structure and its density (usually 3.0 g/cm$^3$ for an Yttrium stabilized $ZrO_2$ ceramic) is less compared to a completely sintered dental ceramic framework (usually 6.1 g/cm$^3$ for an Yttrium stabilized $ZrO_2$ ceramic).

A dental ceramic or dental article is classified as "absorbent", if the dental ceramic is able to absorb a certain amount of a solvent, comparable to a sponge. The amount of solvent which can be absorbed depends e.g. on the chemical nature of the dental ceramic framework, the viscosity of the solvent, the porosity and pore volume of the dental ceramic.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

The "average connected pore diameter" means the average size of the open-celled pores of a material. The average connected pore diameter can be calculated as described in the Examples section.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. The porous ceramic dental material described in the present text does not contain a glass.

"Glass-ceramic" means an inorganic non-metallic material where one or more crystalline phases are surrounded by a glassy phase so that the material comprises a glass material and a ceramic material in a combination or mixture. It is formed as a glass, and then made to crystallize partly by heat treatment. Glass ceramics may refer to a mixture of lithium-, silicon-, and aluminium-oxides. The porous dental material described in the present text does not contain a glass-ceramic.

"Sol" refers to a continuous liquid phase containing discrete particles having sizes in a range from 1 nm to 100 nm.

"Diafiltration" is a technique that uses ultrafiltration membranes to completely remove, replace, or lower the concentration of salts or solvents from solutions containing organic molecules. The process selectively utilizes permeable (porous) membrane filters to separate the components of solutions and suspensions based on their molecular size.

The term "aerogel" shall mean a three-dimensional low density (i.e., less than 20% of theoretical density) solid. An aerogel is a porous material derived from a gel, in which the liquid component of the gel has been replaced with a gas. The solvent removal is often done under supercritical conditions. During this process the network does not substantially shrink and a highly porous, low-density material can be obtained.

"Isotropic sintering behaviour" means that the sintering of a porous body during the sintering process occurs essentially invariant with respect to the directions x, y and z. "Essentially invariant" means that the difference in sintering behaviour with respect to the directions x, y and z is in a range of not more than +/−5% or +/−2% or +/−1%.

The term "tubular reactor" refers to the portion of a continuous hydrothermal reactor system that is heated (i.e., the heated zone). The tubular reactor can be in any suitable shape. The shape of the tubular reactor is often selected based on the desired length of the tubular reactor and the method used to heat the tubular reactor. For example, the tubular reactor can be straight, U-shaped, or coiled. The interior portion of the tubular reactor can be empty or can contain baffles, balls, or other known mixing techniques.

"Casting" means a manufacturing process by which a liquid material (e.g. solution or dispersion) is poured into a mould, which contains a hollow cavity of the desired shape, and then allowed to solidify.

The term "calcining" refers to a process of heating solid material to drive off at least 90 percent by weight of volatile chemically bond components (e.g., organic components) (vs., for example, drying, in which physically bonded water is driven off by heating). Calcining is done at a temperature below a temperature needed to conduct a pre-sintering step.

The terms "sintering" or "firing" are used interchangeably. A pre-sintered ceramic article shrinks during a sintering step, that is, if an adequate temperature is applied. The sintering temperature to be applied depends on the ceramic material chosen.

For ZrO2 based ceramics a typical sintering temperature range is 1100° C. to 1550° C. Sintering typically includes the densification of a porous material to a less porous material (or a material having less cells) having a higher density, in some cases sintering may also include changes of the material phase composition (for example, a partial conversion of an amorphous phase toward a crystalline phase). Sintering of firing means making objects from a compressed powder by heating the material (typically below its melting point—solid state sintering) until its particles adhere to each other.

By "dental milling block" or "dental mill blank" is meant a solid block (3-dim article) of material from which a dental article can be machined. A dental milling block has typically a geometrically defined shape. A dental milling block may have a size of 20 mm to 30 mm in two dimensions, for example may have a diameter in that range, and may be of a certain length in a third dimension. A block or blank for making a single crown may have a length of 15 mm to 30 mm, and a block or blank for making bridges may have a length of 40 mm to 80 mm. A typical size of a block or blank as it is used for making a single crown has a diameter of 24 mm and a length of 19 mm. Further, a typical size of a block or blank as it is used for making bridges has a diameter of 24 mm and a length of 58 mm. Besides the above mentioned dimensions, a dental milling block may also have the shape of a cube, a cylinder or a cuboid. Larger milling blocks may be advantageous if more than one crown or bridge should be manufactured out of one blank. For these cases, the diameter or length of a cylindric or cuboid shaped mill blank may be in a range of 80 to 200 mm, with a thickness being in the range of 10 to 30 mm.

By "machining" is meant milling, grinding, drilling, cutting, carving, or substractive shaping a material by a machine. Milling is usually faster and more cost effective than grinding. A "machinable article" is an article having a 3-dimensional shape and having sufficient strength to be machined.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of the ceramic material can be calculated from the mass of the sample and the density of the used material. The total volume of cells in the sample is assumed to be the remainder of the sample volume (100% minus the total volume of material).

A "powder" means a dry, bulk solid composed of a large number of very fine particles that may flow freely when shaken or tilted.

A "particle" means a substance being a solid having a shape which can be geometrically determined. Particles can typically be analysed with respect to e.g. grain size or diameter.

The mean particle size of a powder can be obtained from the cumulative curve of the grain size distribution and is defined as the arithmetic average of the measured grain sizes of a certain powder mixture. Respective measurements can be done using commercially available granulometers (e.g. CILAS Laser Diffraction Particle Size Analysis Instrument).

Adding an "(s)" to a term means that the term should include the singular and plural form. E.g. the term "additive(s)" means one additive and more additives (e.g. 2, 3, 4, etc.). The term "comprising" includes also the more limited expressions "consisting essentially of" and "consisting of". All single values or values of numerical ranges are deemed to be modified with the term "about".

"Ambient conditions" mean the conditions which the inventive solution is usually subjected to during storage and handling. Ambient conditions may, for example, be a pressure of 900 to 1100 mbar, a temperature of −10 to 60° C. and a relative humidity of 10 to 100%. In the laboratory ambient conditions are adjusted to 23° C. and 1013 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION

In the dental field, water-based colouring liquids are commonly used for colouring especially zirconia based dental framework in a pre-sintered or porous stage. This is typically achieved by dipping the framework into a colouring solution in its entirety. By doing so, a homogenous colour of the whole dental framework is usually achieved.

However, if individual colouration or whitening in small defined areas is desired, the water-based liquids of the prior art cannot be used because the different colours typically will mix up and diffuse into parts of the ceramic article where they are not supposed to be present.

The liquid composition described in the present text solves this problem by allowing a dental technician to selectively apply a whitening agent to parts of the surface of a dental article e.g. by using a brush.

The liquid composition is used for being applied selectively to only parts of the surface of a dental article. That is, the composition is only applied to parts of the surface of the dental ceramic article but not to the whole (inner and outer) surface. In contrast to commercially available colouring liquids, the dental article is not dipped completely into the composition described in the present text.

It was found that the whitening agent remains on the spot or area of the surface where the liquid composition has been applied to and does typically not diffuse through the rest of the material of the porous dental article.

Thus, the invention enables the local and specific application of a whitening agent to selective parts of the surface of a dental article. It allows an exact whitening of individual parts of the surface of a dental article. This may facilitate the imitation of white spots, which can sometimes be found on natural teeth.

If desired, the composition can also be used to apply an opaque surface layer to the inner and/or outer surface of a translucent dental article, especially dental frameworks or dental monolithic ceramic restorations.

The painted features remain essentially sharp, even if the bulk of the dental article is still wet from a previous colouring step.

Thus, the liquid composition can also be applied to the surface of wetted dental article(s), which have already been coloured by using a commercially available water-based colouring liquid, without the risk of the whitening agent spreading indiscriminately due to diffusion.

If desired, the whitening impression produced by the liquid composition in the material can be further adjusted by diluting the liquid composition with a dilution liquid or simply with more solvent.

Moreover, it was found that the liquid composition(s) remain stable over a considerable long period of time. They typically do not show visible (to the human eye) precipitation of the whitening agent during storage at ambient conditions (23° C., normal pressure).

Surprisingly, it has been found that the desired opacifying effect can only be achieved by using a whitening agent with the phosphorous containing components described in the present text, but not by using other components containing sulfate, nitrate, chloride or acetate moieties.

Without wishing to be bound by a certain theory, it is believed that upon contact of the phosphorous containing component of the whitening agent with the zirconia of the porous dental article, a reaction takes place, which after sintering may result in a different crystal phase of the zirconia material.

It was found that for whitening agent(s) comprising phosphorous containing component(s) the interaction between the zirconia takes place in particular in the surface region. Thus, the whitening agent essentially remains on that location to which it has been applied and does not migrate into the remaining part of the porous zirconia article.

Other embodiments, features and advantages of the present invention will be apparent from the following detailed description, drawings, and claims.

The liquid composition typically has an adequate viscosity so that a sufficient amount of composition can be applied to the surface of the porous dental article.

According to one embodiment, the liquid composition has a viscosity above 10 or above 50 or above 100 mPa*s (measured at 23° C. with a shear rate of 50 s$^{-1}$). The viscosity of the composition is typically below 10,000 or below 5,000 or below 2,000 mPa*s (measured at 23° C. with a shear rate of 50 s$^{-1}$).

Typical viscosity ranges include from 10 to 10,000 or from 20 to 8,000 or from 50 to 5,000 mPa*s (measured at 23° C. with a shear rate of 50 s$^{-1}$).

If the viscosity of the composition is too high, the whitening agent might not be able to enter the pores of the ceramic material at all. On the other hand, if the viscosity of the composition is too low, the whitening agent might diffuse through the pores too much.

If desired, the measurement of the viscosity can be done as follows: A viscosimeter MCR300 (from Anton Paar Comp.) is used. A portion of the composition is placed between two steel discs with a diameter of 8 mm and a gap of 1 mm at a temperature of 23° C. The gap is filled completely with the composition. Excess composition is removed. The shear rate between the rotating discs d(gamma)/dt is set constantly to 50 s$^1$. The measurement is done 500 s after starting the shearing process of the composition.

Thus, the composition is in the form of a liquid which can be applied onto the surface of either a dry or wet, optionally pre-coloured, porous zirconia based dental article.

If the porous zirconia article is already wetted, the composition will solve into the geometry within minutes and disappear from the surface.

If the liquid composition is used in excess, not all of it will migrate into the pores of the porous zirconia based material. The composition remaining on the surface can be wiped off, if desired, before or after sintering without problems. In one embodiment the composition is transparent.

A composition can be characterized as transparent within the meaning of the invention if a beam of visible light (400 to 700 nm) is not scattered by the solution and the solution does not appear to be turbid. Providing a transparent composition can be desirable in that the whitening agent being contained in the composition is either a real solution (e.g. dissociation into ions) or a dispersion (e.g. particle size smaller than wavelength of visible light).

The liquid composition described in the present text comprises a whitening agent.

The whitening agent comprises a phosphorous containing component.

The phosphorous containing component comprises a phosphate, phosphone or phosphine moiety. The whitening agent is typically water-soluble. The whitening agent can be a liquid or a solid (e.g. salt).

Examples of phosphorous containing components include acids and salts comprising one or more phosphate, phosphone or phosphine moieties and mixtures of acids and salts thereof.

At least one P—O unit of the phosphate, phosphone or phosphine moiety needs to be dissociable or able to otherwise interact with zirconia, e.g. by forming a complex.

According to one embodiment, the phosphorous containing component is characterized by formula (1):

$$(R1O)(R2)(R3)P=X, \qquad (1)$$

with X being O or S,

R1 being H, NH$_4$, a metal ion (e.g. Na, K or Li) or an organic moiety (including C1 to C4 alkyl, phenyl, acetoxy), R2 and R3 being independently selected from R1 or OR1, with the proviso that at least one residue R1, R2 or R3 is able to dissociate from O in the liquid composition (e.g. H, NH$_4$, Na) or comprises an oxygen-containing functional group which can interact with a zirconia material (e.g. carboxyl group like OAc).

The whitening agent is typically present in the liquid composition in the following amounts:
Lower amount: at least 5 or at least 10 or at least 20 wt.-%;
Higher amount: up to 60 or up to 50 or up to 40 wt.-%;
Range: from 5 to 60 or from 10 to 50 or from 20 to about 40 wt.-%; wt.-% with respect to the amount of the liquid composition.

If the amount of whitening agent contained in the liquid composition is too low, the effects obtained in the sintered ceramic article might be too weak for the intended use.

If, however, the amount of whitening agent contained in the liquid composition is too high, the composition might become too viscous or acidic. In addition, properties of the ceramic article, like e.g. strength, might be influenced in an undesired manner.

Specific examples of the phosphorous containing component include H3PO4, alkaline (e.g. Li, Na, K) and ammonium salts of H3PO4, phosphoric esters (including phosphoric esters containing saturated or unsaturated organic moieties like phosphoric acid monoethyl ester, phosphoric acid diethyl ester, phosphoric acid di-propylester mono ammonium salt) and mixtures thereof.

If the whitening agent is already in a liquid stage (e.g. an aqueous solution of a phosphorous containing component like an aqueous phosphoric acid), the liquid composition can be identical with the whitening agent.

Besides the whitening agent, the liquid composition may further comprise a liquid or solvent. According to one embodiment, the solvent is water. According to another embodiment, the solvent is different from water. The liquid or solvent is typically miscible with water.

According to one embodiment, the solvent may be characterized by at least one of the following features:
molecular weight (Mw): from 18 to 1,000 g/mol or from 60 to 400 g/mol;
viscosity: from 1 to 2,000 mPa*s or from 10 to 1,500 mPa*s or from 100 to 1,000 mPa*s (measured at 23° C. at a shear rate of 50 s$^{-1}$);
free of polymerizable groups like (meth)acrylate groups, epoxy groups, carbon-carbon unsaturated groups.

Mw (substance) is the average molecular weight of the respective polymer used.

Liquids which can be used include polyalcohols including ethylene glycol, polyethylene glycols, glycerol and mixtures thereof.

Polyethylene glycols which can be used can be represented by formula (2)

$$R1O—(CH2-CH2-O)m-R1 \qquad (2)$$

with R1=H, Acyl, Alkyl, Aryl, Alkylaryl, Polypropylglycol, Poly-THF, preferably H, Acetyl, Methyl, Ethyl, Propyl, Butyl, Hexyl, Octyl, Nonyl, Decyl, Lauryl, Tridecyl, Myristyl, Palmityl, Stearyl, Oleyl, Allyl, Phenyl, p-Alkylphenyl, Polypropyleneglycol, Poly-THF and m=2 to 100, preferably 2 to 20, more preferably 2 to 5

The average molecular weight (Mw) of the polyethylene glycol should be in the range of 100 to 5.000, preferably in the range of 100 to 1.000, more preferably in the range of 100 to 300.

If desired, the average molecular weight (Mw) can be determined according to procedures known to a person skilled in the art as described for example in Arndt/Müller, Polymercharakterisierung, Hanse Verlag, 1996. Depending on the molecular weight to be determined, it might be necessary to apply different measurement methods (see below).

Most PEGs (polyethylene glycols) include molecules with a distribution of molecular weights, i.e. they are polydisperse. The size distribution can be characterized statistically by its weight average molecular weight (Mw) and its number average molecular weight (Mn), the ratio of which is called the polydispersity index (Mw/Mn). Mw and Mn can be measured by mass spectroscopy.

Specific examples of water-miscible solvent(s), which can be used, include polyol(s) (including polyvinyl alcohol), glycol ether(s) (e,g, PEG 200, PEG 400, PEG 600, diethylene glycol methyl ether, diethylene glycol ethyl ether), alcohol(s) (including 1,2-propanediol, 1,3-propanediol, ethanol, (n- and iso-)propanol, glycerol), glycerol ether, and mixtures thereof.

In particular, the following solvents were found to be useful: glycerol, ethylene glycol, propylene glycol and mixtures thereof. According to one embodiment, the solvent should be able to dissolve the whitening agent. Dissolving means that the composition does not contain particles being visible to the human eye.

The amount of solvent used is not particularly limited unless the result to be achieved cannot be obtained.

The liquid can be used in an amount of at least 20 or at least 50 or at least 70 wt.-% with respect to the whole weight of the liquid composition.

There is no particular upper amount, however, the liquid is typically used up to an amount of up to 98 or up to 96 or up to 90 wt.-% with respect to the whole weight of the liquid composition.

Useful ranges for the liquid include from 20 to 98 wt.-% or from 50 to 96 wt.-% or from 70 to 90 wt.-% with respect to the whole weight of the liquid composition.

The liquid composition may also contain one or more additive(s).

Additives which can be added to the composition include stabilizers (such as methoxy phenol hydrochinone, Topanol A, ascorbic acid and mixtures thereof), buffers (such as acetate or amino buffers and mixtures thereof), preservative agents (such as sorbic acid or benzoic acid and mixtures thereof), soluble colourants (e.g. colourants which can be added to food) and mixtures thereof.

Adding soluble colourants can be beneficial in order to enhance the visibility of the composition during use, especially, if the composition is transparent. Thus, the practitioner can easily determine to which parts of the surface of the dental ceramic the composition has already been applied and which parts have not been treated yet and should remain untreated.

On the other hand the soluble colourants which are typically of organic nature will be burnt during a later sintering step and thus not be incorporated into the crystal structure of the dental ceramic.

Examples of soluble colourants which can be used include Riboflavin (E101), Ponceau 4R (E124), Green S (E142).

There is no need for additive(s) to be present, however, if they are present, they are typically present in an amount which is not detrimental to the purpose to be achieved when applying the composition.

If additive(s) are present, they are typically present in an amount of 0.01 to 10 wt.-% or from 0.05 to 5 wt.-% or from 0.1 to 3 wt.-% with respect to the whole composition.

According to one embodiment, the liquid composition comprises the respective components in the following amounts:

Whitening agent(s): from 5 to 60 or from 6 to 50 or from 7 to 40 wt.-%;
Liquid(s): from 20 to 98 or from 50 to 96 or from 70 to 90 wt.-%;
Additive(s): from 0 to 10 or from 0.05 to 5 or from 0.1 to 3 wt.-%;

wt.-% with respect to the amount of the liquid composition.

The liquid composition can be produced by simply mixing the components contained therein until a homogeneous mixture is obtained.

The liquid composition described in the present text is applied to the surface of a porous dental article comprising or preferably consisting essentially of zirconia.

The term "consisting essentially of" means that the major part (e.g. greater than 80 or 85 or 90 wt.-%) of the dental ceramic is based on ZrO2. The rest may be comprised of oxides selected from $HfO_2$ and stabilizers including Y2O3, CaO, MgO, CeO2 or mixtures thereof.

The dental article to which the liquid composition is to be applied is porous. Moreover, the dental article has an outer and an inner surface. The outer surface typically has typically an overall convex shape, whereas the inner surface typically has an overall concave shape. The dental ceramic onto which the solution is applied can be dry or wet.

"Wet" means that the ceramic material still contains a small amount of water. However, there should be no visible spots of water residues on the surface.

A pre-sintered or porous material sample is considered wet, if the material has been completely dipped into water for 10 s, removed from the water and wrapped for 10 s into a paper tissue being able to absorb water or alternatively, if a water-based solution has been applied to large areas of the material using e.g. a sponge, a brush, etc.

The surface of a pre-sintered or porous material sample is considered dry, if the material has been completely dipped into a water-based solution for 10 s, removed from the water, wrapped for 10 s into a paper tissue being able to absorb water and placed into an oven for 1 h at a temperature of 200° C. or left to dry open to the air for 4 h, or if no water-based solution has been applied to the pre-sintered or porous ceramic at all.

According to one embodiment, the porous dental article is a ZrO2 based article which is stabilized with Y2O3. The dental article is typically in a pre-sintered stage.

Porous dental zirconia articles can be obtained e.g. by pre-sintering a compressed zirconia powder.

Porous dental zirconia articles compositions are known to the skilled person in the art (examples are described e.g. in WO 00/46168 A1).

Yttrium doped tetragonal stabilized zirconia powder is sometimes also referred to as YTZP powder and commercially available from e.g. Tosoh Comp., Japan.

The pressure to be applied is typically in the range of 150 to 200 MPa. Alternatively, the applied pressure is set so that the pressed body reaches a certain density, e.g. in the case of a zirconia body, a density from 2.8 to 3.2 g/cm3.

The porous zirconia article obtained according to the above process can be characterized by at least one of the following features:
(a) Not showing a $N_2$ adsorption and/or desorption isotherm with a hysteresis loop;
(b) BET surface: from 2 to 20 $m^2/g$ or from 3 to 14 $m^2/g$;
(c) biaxial flexural strength: from 8 to 80 or from 20 to 50 MPa;
(d) x, y, z dimension: at least 5 mm or at least 10 or at least 20 mm.

According to another embodiment, the porous dental article is a $ZrO_2$ based article shows a N2 adsorption and/or desorption of isotherm type IV.

Commercially available Y-TZP ceramic materials typically show a N2 adsorption and/or desorption of isotherm type II (according IUPAC classification), which was found to be less effective for producing an aesthetic dental article in an efficient way.

Materials showing a type II isotherm are said to be macro-porous, whereas materials showing a type IV isotherm are said to be meso-porous.

The liquid composition is typically absorbed very quickly, but having the effect that the diffusion of the whitening agent is essentially limited to those areas to which the liquid composition has been applied.

If desired, the dental ceramic article described in the present text can be further individualized manually, e.g. using a file, a cutter or carving tool, if desired. The material (before sintering) is sufficiently hard to allow a precise machining but not too hard or too strong to prevent manually individualization. In contrast to this, commercially available zirconia materials are often too soft and thus allow no precise carving or modelling in a pre-sintered stage.

The zirconia material described in the present text shows a variety of well balanced features (e.g. sufficient strength to be machined, adequate strength to be manually individualized, reduced wear of machining tools and/or reduced production of dust during machining) In contrast to zirconia material described in the art, the zirconia material described in the present text is more translucent after sintering. A whitening composition applied to this material will thus become better visible compared to whitening compositions applied to less translucent or more opaque zirconia material. The porous zirconia article shows a N2 adsorption and/or desorption of isotherm type IV according to IUPAC classification.

Further, the porous zirconia article typically has a Vickers hardness from 25 to 150 or from 35 (HV 0.5) to 150 (HV 1).

According to one embodiment, the porous zirconia article described in the present text can be characterized by at least one of the following features:
(a) showing a $N_2$ adsorption and/or desorption isotherm with a hysteresis loop;
(b) showing a $N_2$ adsorption and desorption of isotherm type IV according to IUPAC classification and a hysteresis loop;
(c) showing a $N_2$ adsorption and desorption isotherm of type IV with a hysteresis loop of type H1 according to IUPAC classification;
(d) showing a $N_2$ adsorption and desorption isotherm of type IV with a hysteresis loop of type H1 according to IUPAC classification in a $p/p_0$ range of 0.70 to 0.95;
(e) average connected pore diameter: from 10 to 100 nm or from 10 to 80 nm or from 10 to 70 nm or from 10 to 50 nm or from 15 to 40;
(f) average grain size: less than 100 nm or less than 80 nm or less than 60 nm or from 10 to 100 or from 15 to 60 nm;
(g) BET surface: from 10 to 200 $m^2/g$ or from 15 to 100 $m^2/g$ or from 16 to 60 $m^2/g$;
(h) biaxial flexural strength: from 10 to 40 or from 15 to 30 MPa;
(i) Vickers hardness: from 25 (HV 0.5) to 150 or from 35 to 140 (HV 1).
(j) x, y, z dimension: at least 5 mm or at least 10 or at least 20 mm.

A combination of the following features was found to be particularly beneficial: (a) and (h), or (a) and (b) and (h), or (b) and (c), or (c), (e), (g) and (h). If desired the above features can be determined as described in the Example section.

The BET surface of porous zirconia materials described in the prior art is typically within a range from 2 to 9 $m^2/g$, whereas the BET surface of the porous zirconia materials described in the present text is preferably above 10 $m^2/g$.

The average grain size of the zirconia particles in the porous zirconia article described in the present text is small compared to the average grain size of the material of commercially available zirconia materials.

A small grain size can be beneficial in that it typically leads to a more homogeneous material (from a chemical perspective), which may also result in more homogeneous physical properties. Useful ranges for the x, y and z dimensions include from 5 to 300 or from 8 to 200 mm.

It was found that it is beneficial for certain properties, if the porous zirconia material has a certain average connected pore diameter. The average connected pore diameter should be in a particular range. It should not be too small and also not be too large.

The porous zirconia material described in the present text and used for providing the porous dental ceramic article has a smaller average connected pore diameter than porous zirconia ceramic material obtained by compacting zirconia powder, like 3Y-TZP powder from Tosoh Comp.

Due to the nano-scaled particle size and specific average connected pore diameter of the material used for producing the porous zirconia ceramic material of the porous dental ceramic article, this material has a different sintering behaviour compared to the zirconia ceramic material of dental materials which are commercially available (e.g. LAVA™ Frame from 3M ESPE) and other zirconia ceramics available on the dental market being typically produced by compacting and pressing zirconia powder (e.g. 3Y-TZP zirconia powder from Tosoh Comp.).

The Vickers hardness of the material is in a particular range. If the Vickers hardness of the material is too low, the machinability could fall off in quality (edge chipping or breaking of the workpiece) as well as in the ease of manual reworking to individualize the frame of a dental restoration or a monolithic restoration as well. If the Vickers hardness of the material is too high, the wear of the machining tools may increase in an uneconomic range or the tool could break and destroy the workpiece. The biaxial flexural strength of the material is typically also in a particular range.

It was found that if the biaxial flexural strength of the material is too low, the material tends to crack during the milling process or during the manual finishing by a dental technician.

On the other hand, if the biaxial flexural strength of the material is too high, the processing of the material by a milling machine is often not possible with reasonable efforts. The milling tool used or the milled material often tend to chip or break. In such a case the shaping of the material had to be done by grinding, e.g. using a Cerec™ grinding machine (Sirona).

The material of the porous zirconia ceramic article can be characterized by at least one of the following features:
- ZrO2 content: from 70 to 98 mol % or from 80 to 97 mol %;
- HfO2 content: from 0 to 2 mol % or from 0.1 to 1.8 mol %;
- Y2O3 content: from 1 to 15 mol % or from 1.5 to 10 mol % or from 2 to 5 mol %;
- Al2O3 content: from 0 to 1 mol % or from 0.005 to 0.5 mol % or from 0.01 to 0.1 mol %.

According to a further embodiment, the porous zirconia article has a composition being characterized by the following features:
- ZrO2 content: from 90 to 98 mol %,
- HfO2 content: from 0 to 2 mol %,
- Y2O3 content: from 1 to 5 mol %,
- Al2O3 content: from 0 to 0.1 mol %.

It was found that a higher Y2O3 content typically leads to an increase of the cubic crystal phase in the zirconia ceramic material after sintering the material to final density. A higher content of the cubic crystal phase may contribute to a better translucency.

According to a particular embodiment the porous zirconia article can be characterized by the at least one or more or all of the following features:
- showing a N2 adsorption of isotherm type IV according to IUPAC classification,
- showing a N2 adsorption with a hysteresis loop in a p/p0 range of 0.70 to 0.95,
- average connected pore diameter: from 15 to 60,
- average grain size: less than 100 nm,
- BET surface: from 15 to 100 m$^2$/g or from 16 to 60 m$^2$/g,
- Biaxial flexural strength: from 10 to 40 MPa,
- x, y, z dimension: at least 5 mm,
- Vickers hardness: from 25 to 150, and
- Density: from 40% to 60% of theoretical density.

The zirconia ceramic dental article described herein may have an x, y, and z dimensions of at least 3 mm (in some embodiments, at least 5 mm, 10 mm, 15 mm, 20 mm, or even 25 mm) and a density of at least 98.5 (in some embodiments, 99, 99.5, 99.9, or even at least 99.99) percent of theoretical density, wherein at least 70 mole percent of the crystalline metal oxide is $ZrO_2$, and wherein the $ZrO_2$ has an average grain size less than 400 nanometers (in some embodiments, less than 300 nanometers, 200 nanometers, 150 nanometers, 100 nanometers, or even less than 80 nanometers).

The zirconia material of the porous dental ceramic article described in the present text can be obtained by a process comprising the step of heat treating or calcining a zirconia aerogel.

The zirconia aerogel can typically be characterized by at least one of the following features:
a. comprising crystalline zirconia particles having an average primary particle size in a range from 2 nm to 50 nm or from 2 nm to 30 nm or from 2 to 20 or from 2 to 15 nm;
b. content of crystalline zirconia particles: at least 85 mol.-%;
c. having an organic content of at least 3 wt.-% or within a range from 3 to 10 wt.-%;
d. x, y, z dimension: at least 5 or at least 8 or at least 10 or at least 20 mm.

A combination of the features [(a), (b)] or [(a), (c)] or [(a), (b), (c)] or [(a), (b), (c), (d)] can be preferred.

The heat treatment of the zirconia aerogel for obtaining the porous zirconia article is typically done under the following conditions:
- temperature: from 900 to 1100° C. or from 950 to 1090° C.; from 975 to 1080° C.;
- atmosphere: air or inert gas (e.g. nitrogen, argon);
- duration: until a density of 40 to 60% of the final density of the material has been reached.

The heat treatment or calcining can be conducted in one or more steps.

In a first heat treatment step a binder burn-out could be performed to remove all organic additives from previous process steps to obtain a so called "white body". In a second heat treatment step the strength and/or the hardness of the white-body could be adjusted to the needs of the follow up processes like machining In case of a machinable blank the sintering protocol should reflect the interaction of temperature with strength and/or hardness.

If the temperature is too low, the hardness and/or strength of the resulting article might be too low. This can cause problems during a later machining step, e.g. with respect to chipping.

If, on the other hand, the temperature is too high, the hardness and/or strength of the material may become too high. This can cause problems during a later machining step as well, e.g. with respect to the machining tool durability.

The dwell time (that is the time during which the aerogel is kept at that temperature) is helpful as well to tune strength and/or hardness to the specific needs of the chosen machining technology. The dwell time, however, can also be in a range from 0 to 24 h or from 0.1 to 5 h.

If the dwell time is too long, the dental mill blanks may become too hard to be machined under reasonable conditions.

According to one embodiment, the porous zirconia article can be obtained by a process comprising the steps of
- providing a zirconia sol comprising crystalline metal oxide particles and a solvent;
- optionally concentrating the zirconia sol to provide a concentrated zirconia sol;
- mixing the sol with a polymerizable organic matrix (e.g. adding a reactive surface modifier to the zirconia sol and optionally an initiator being able to polymerizable surface-modified particles of the zirconia sol);
- optionally casting the zirconia sol into a mould to provide a casted zirconia sol,
- curing the polymerizable organic matrix of the zirconia sol to form a gel (sometimes also referred to as gelation step);
- removing the solvent from the gel (e.g. by first removing water, if present, from the gel via a solvent exchange process to provide an at least partially de-watered gel; followed by a further extraction step where the remaining solvent is extracted e.g. via super critical extraction) to provide the aerogel;
- optionally cutting the aerogel into smaller pieces;
- heat-treating the aerogel to obtain a machinable porous zirconia material or article.

The process of producing the porous ceramic zirconia material typically starts with providing a sol of $ZrO_2$ particles.

To the sol of $ZrO_2$ particles a surface-modifying agent is added, preferably a crosslinkable surface-modifying agent (e.g. a radically reactive surface modifier).

The $ZrO_2$ particles having been surface-modified with a crosslinkable agent can be polymerized, if desired, to provide a composition comprising crosslinked $ZrO_2$ particles.

The crosslinkable surface-modifying agent can be removed later, e.g. during a calcining and/or pre-sintering step.

If desired, the sol is casted into a mould. The mould may have the negative shape of the dental mill block to be provided. Due to size reduction which may be caused by heat treatments of the material, the size of the mould is typically larger than the size of the final dental mill blank. The shape of the mould is not particularly limited.

The casted zirconia sol is typically treated with heat or radiation in order to start polymerization of the reactive surface modifier. This process usually results in a gel. If present and desired, water may be removed from the gel, at least partially.

Remaining solvent of the above described sol/gel process is removed, e.g. by supercritical extraction techniques resulting in an aerogel (e.g. in block form). If desired, the aerogel may be cut into smaller pieces, e.g. having the shape of the dental mill blank.

According to a further embodiment, the invention is directed to a kit of parts comprising
- at least one receptacle containing the liquid composition as described in the present text;
- a porous dental mill blank useful for producing the porous dental zirconia article as described in the present text;
- optionally at least one receptacle containing a colouring liquid;
- optionally application and mixing appliances;
- optionally an instruction of use describing the process steps to be conducted to obtain a partially opacified dental restoration.

Examples of receptacles include bottles, wells, tubes and vessels.

Colouring solutions for dental ceramics are meanwhile well known in the art. Examples of colouring solutions are described in U.S. Pat. No. 6,709,694, US 2006/0117989, WO 2009/014903, EP application No. 11177189. The content of these references is herewith incorporated by reference.

Theses colouring liquids typically comprise water, metal cations selected from rare earth elements, transition metal and mixtures thereof (including cations of Fe, Mn, Er, Pr and mixtures thereof), and sometimes a complexing agent or further additives like (poly)ethylene glycol. The colouring liquids are typically used for homogeneously colouring dental ceramics and in particular porous dental ceramic framework.

The liquid or solvent being provided in a separate receptacle enables the practitioner to further individualize or dilute the composition, especially with respect to its intensity.

Examples of application appliances include brushes, sponges, (hollow) needles, etc.

Examples of mixing appliances include mixing wells, trays, plates, slides, etc.

Sometimes it is desirable to not only apply the liquid composition containing a whitening agent as described in the present text to the dental zirconia article, but also to colour the dental zirconia article.

Experiments have shown that the whitening agent described in the present text is typically not compatible with the metal cations contained in a typical colouring liquid to form a storage stable composition.

Thus, the respective liquids or compositions not only need to be kept separate before use, but also need to be applied in separate steps. This issue can be addressed with the device as described below.

According to a further embodiment, the invention is thus directed to a device comprising
- at least one compartment (A) containing the liquid composition as described in the present text;
- at least one compartment (B) containing a colouring liquid as described in the present text; and
- an instruction of use describing process steps to be conducted to obtain a partially opacified dental zirconia article;

compartment (A) and compartment (B) being separated from each other by a pre-defined break zone.

Using such a device is beneficial because it allows reducing the application steps typically needed for obtaining a partially coloured and opacified or whitened dental zirconia article. The application of the whitening agent and a colouring liquid or agent can be combined in one step.

On the one hand, the device described in the present text is suitable to keep the respective liquids or compositions separate during storage, and on the other hand it enables the practitioner to mix them shortly before use.

Further, due to the pre-defined volume of the respective compartments, the mixing ratio is defined as well resulting in a reproducible and homogeneous mixture.

It also allows including the desired type of application device (e.g. brush or sponge) for the composition to be applied.

Compartment (A) and compartment (B) of the device are arranged to allow mixing of the respective liquids or compositions contained therein to obtain a coloured composition comprising the whitening agent. The device may optionally contain an application device like a brush tip or sponge tip for applying the mixture.

Figure 2:
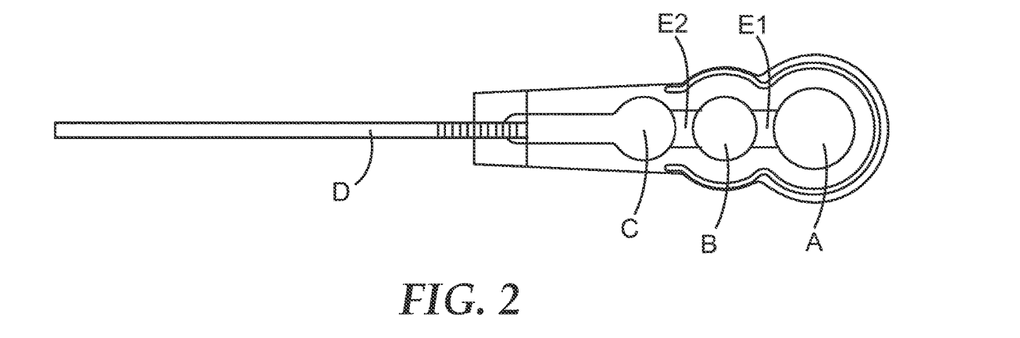
FIG. 2 shows a device enabling the practitioner to provide and apply a liquid composition as described in the present text comprising in addition a colouring liquid.

A suitable device is shown in FIG. 2. The device has at least two compartments (A) and (B). Compartment (A) is for receiving or containing the liquid composition described in the present text. Compartment (B) is for receiving or containing a colouring liquid as described in the present text. The compartments are separated from each other by a pre-defined break zone (E1) which can be opened upon asserting pressure on either of the compartment. Upon asserting pressure on compartment (A), the pre-defined breaking zone is opened and the composition or liquid contained in compartment (A) flows into compartment (B). The composition or liquid contained in compartment (B) is then mixed with the composition or liquid which was contained in compartment (A).

The device further comprises a pocket (C) separated from compartment (B) by a pre-defined break zone (E2) similar to the pre-defined break zone between compartments (A) and (B).

Upon asserting pressure on compartment (B) and optionally also on compartment (A), the pre-defined breaking zone (E2) to the pocket is opened and the mixture flows into the pocket (C) from which it can be delivered or applied to the desired part(s) of the surface of the porous dental zirconia article.

Delivery or application of the mixture (i.e. coloured liquid composition) can be effected by a brush or sponge tip (D) which can be contained in the pocket or which can be placed into the pocket, if desired.

Examples of devices which can be used for providing a coloured liquid composition obtained by mixing the liquid composition described in the present text and a colouring liquid are described in U.S. Pat. No. 6,105,761 (Peuker et al.) and U.S. Pat. No. 7,097,075 (Peuker et al.). The content of these references is herewith incorporated by reference.

Selectively applying the liquid composition to the surface of the dental article is usually achieved by painting e.g. using a brush. However, the composition can also be applied by using brushes, sponges, (hollow) needles, pens, and by spraying.

The liquid composition is typically stored in a container or receptacle before use. Suitable containers include vessels, bottles and sealed wells According to one embodiment the liquid composition is applied to the surface of the dental zirconia article with a pen, the pen comprising a housing, a brush tip, a removable cap and a reservoir for storing the liquid composition described in the present text.

The brush tip is typically attached or fixed to the front end of the housing. The reservoir is typically fixed or attached to the rear end of the housing. The removable cap is typically used for protecting the brush tip during storage.

Using a pen may facilitate the application of the liquid composition and will help the practitioner to save time. Further, a pen with a cap will prevent the pen from drying out if not used. The volume of the reservoir may be in a range from 1 ml to 10 ml or from 2 ml to 5 ml. The reservoir may be removable or fixed to the housing of the pen.

The brush tip typically comprises bristles. The material the bristles are made of can be selected from artificial or natural materials. Artificial materials include polyamides (nylon), polyesters and mixtures thereof. Natural materials usually include different kinds of animal hair. The brush tip may be removable or exchangeable, too.

The length of the brush tip extending from the pen is typically within a range from 5 to 20 mm or from 8 to 15 mm. If the bristles are too short, application of the solution to the inside of a dental restoration may be difficult. If, on the other hand, the bristles are too long, the handling of the brush itself might become impractical for dental applications.

The thickness of the brush tip at its base is typically in the range from 0.3 to 5 mm or from 1 to 4 mm. If the tip is too broad, application of the solution to the inside of a dental restoration may be difficult. If, on the other hand, the tip is too narrow, the handling of the brush itself might become impractical for dental applications.

Furthermore, if the length and the thickness of the brush tip is either too low or too high, it will be difficult to apply the solution properly, that is either too little to too much of the solution is applied. Both may be detrimental for achieving the desired effect.

The shape of the brush tip should be tapered and fan out, if desired, when pressure is applied. Thus, the brush tip should have some flexibility. A brush tip with these properties can be used to draw thin lines and also to paint on larger areas.

A combination of a brush tip comprising bristles having a length from 8 to 15 mm with the solution described in the present text having a viscosity above 200 mPa*s or above 500 mPa*s (measured at 23° C.) was found to be beneficial. Such a combination facilitates the accurate application of the solution on the surface of the porous dental ceramic(s).

Thus, the invention may also be directed to a pen as described in the present text comprising the liquid composition comprising the whitening agent. Drying the surface of the dental article to which the liquid composition has been applied is not absolutely necessary, but can be preferred to reduce the time needed for firing the dental article later.

Drying can be effected by simply storing the dental ceramic e.g. on a plate at ambient conditions for a couple of hours (1 to 3 h). If, however, a high boiling solvent is used, drying might be difficult to achieve.

The invention is also directed to a dental zirconia article obtainable by a process as described in the present text. The dental zirconia article may have the shape of a crown, bridge, inlay, onlay, veneer, facing, coping, crown or bridged framework, implant, abutment, orthodontic appliances and parts thereof.

A dental article having being treated according to the above described process steps is different from dental ceramics which have been treated with essentially water-based colouring or whitening solutions of the state of the art.

Applying water-based colouring or whitening solutions to the surface of dental ceramics typically leads to diffuse colouring or whitening of the whole dental ceramic, whereas the inventive composition allows for a more accurate, well defined whitening effect.

If desired, the extent of diffusion of the composition on the surface of the treated dental ceramic can be determined as follows:

The width of a line drawn with the inventive composition can be visually confirmed after sintering. More accurately, X-ray fluorescence (XRF) measurements can be conducted in micro mapping mode to determine the line's width, i.e. scanning the surface of the ceramic in e.g. 0.25 mm steps and measuring only small spots of e.g. 0.5 mm diameter.

A width of e.g. 0.5 mm of the drawn structures is considered to meet the expectations of a dental technician in most cases for an effect agent being applied to only selective parts of the surface of a dental ceramic.

A typical process of producing a zirconia ceramic dental article comprises the steps of a) providing a dental mill blank comprising a porous zirconia material,
b) placing the dental mill blank in a machining device,
c) machining the porous zirconia material to obtain a machined porous zirconia dental article, the machined porous zirconia dental article having the shape of a crown, bridge, inlay, onlay, veneer, facing, coping, crown and bridged framework, implant, abutment, orthodontic appliances (e.g. brackets, buccal tubes, cleats and buttons) or parts thereof,
d) applying the liquid composition described in the present text to only some parts of the outer and/or inner surface of the machined porous zirconia dental article, in particular to the inner surface thereof,
e) optionally drying the machined porous zirconia dental article,
f) optionally sintering the machined porous zirconia dental article.

The process of producing the dental zirconia article may further comprise the step of firing or sintering the porous dental zirconia article having been treated with the liquid composition. The firing conditions are typically dependent on the ceramic material used.

The firing usually takes place for a $ZrO_2$ based ceramic at a temperature above 1300° C., preferably above 1400° C., more preferably above 1450° C. and lasts for at least 0.5 h, preferably for at least 1 h, more preferably for at least 2 h.

The firing will result in a zirconia ceramic dental article, sometime also referred to as crystalline metal oxide article.

If conducted, the firing or sintering step should be accomplished under conditions which results in a dental ceramic article having an acceptable tooth like colour (e.g. a colour which fits into the Vita™ shade guide).

Useful sintering conditions can be characterized by one or more of the following parameters:
- temperature: from 900 to 1500° C. or from 1000 to 1400° C. or from 1100° C. to 1350° C. or from 1200° C. to 1400° C. or from 1300° C. to 1400° C. or from 1320° C. to 1400° C. or from 1340° C. to 1350° C.
- atmosphere: air or inert gas (e.g. nitrogen, argon);
- duration: until a density of 95 or 98 or 99 to 100% of the final density of the material has been reached;
- dwell time: from 1 to 24 h or from 2 to 12 h;
- pressure: ambient pressure.

A furnace which can be used is the commercially available Lava™ Therm (3M ESPE).

During the firing process the porous dental ceramic article is sintered to its final shape, thereby undergoing changes with regard to dimension, density, hardness, bending strength and/or grain size.

The dwell time (that is the time during which the article is kept at that temperature) is not really critical. The dwell time can be zero. The dwell time, however, can also be in a range from 0 to 24 h or from 0.1 to 5 h.

The firing temperature and dwell time (that is, the time period during which a particular temperature is kept) are typically correlated. A higher temperature typically requires only a short dwell time. Thus, the dwell time, may last from 0 (e.g. if the firing temperature is 1550° C.) to 10 h (e.g. if the firing temperature is 1100° C.) or from 0.1 to 8 h.

Generally, the sintering or firing conditions are adjusted such that the sintered dental ceramic article has a density of equal or greater than 98% compared with the theoretically achievable density.

After sintering, the dental article can typically be characterized by at least one or more or all of the following features:
- density: fully sintered density of at least 98.5 (in some embodiments, 99, 99.5, 99.9, or even at least 99.99) percent of theoretical density;
- phase content tetragonal phase: from 1 to 100 wt.-% or from 10 to 100 wt.-%; cubic phase: from 30 to 100 wt.-% or from 50 to 90 wt.-%;
- biaxial flexural strength: from 450 MPa to 2200 MPa, or from 500 MPa to 2000 MPa.

Thus, the present invention is also directed to a dental zirconia article obtainable or obtained by a process as described in the present text, the dental zirconia article having the shape of a crown, bridge, inlay, onlay, veneer, facing, coping, crown or bridged framework, implant, abutment, orthodontic appliances and parts thereof.

In contrast to dental zirconia articles which are already available, the dental zirconia article described in the present text and obtained or obtainable by the process described in the present text comprises opaque spots or areas of its inner and/or outer surface.

According to a further embodiment, the process described in the present text comprises the steps of:
a) providing a liquid composition and a porous 3-dimensional dental zirconia article having an outer and inner surface (e.g. as described in the present text),
b) applying the liquid composition to only a part of the inner and/or outer surface of the porous dental zirconia article,
c) optionally drying the porous dental zirconia article, and
d) optionally firing the porous dental zirconia article,
the liquid composition comprising a whitening agent comprising at least one phosphate moiety and having a viscosity from 10 mPa*s to 10,000 mPas*s at 23° C.,
the liquid composition being essentially free of the following components:
- filler,
- colouring ions selected from iron, erbium, praseodymium or mixtures thereof,
- reactive organic monomers, the porous dental zirconia article being characterized by the following features:
- showing a N2 adsorption of isotherm type IV according to IUPAC classification,
- showing a N2 adsorption with a hysteresis loop in a p/p0 range of 0.70 to 0.95,
- average connected pore diameter: from 15 to 60 nm,
- average grain size: less than 100 nm,
- BET surface: from 15 to 100 $m^2/g$ or from 16 to 60 $m^2/g$,
- Biaxial flexural strength: from 10 to 40 MPa,
- x, y, z dimension: at least 5 mm,
- Density: from 40% to 60% of theoretical density,
- $ZrO_2$ content: from 90 to 98 mol %,
- $HfO_2$ content: from 0 to 2 mol %,
- $Y_2O_3$ content: from 1 to 5 mol %,
- $Al_2O_3$ content: from 0 to 0.1 mol %, the optional firing step being conducted under the following conditions:
- temperature: from 1200° C. to 1400° C.,
- atmosphere: air or inert gas,
- duration: until a density of at least 95 or at least 98 of the final density of the material has been reached,
- dwell time: from 1 to 24 h,
- pressure: ambient pressure.

The liquid composition described in the present text does typically not contain components which might produce a toxic, injurious, or immunological response in living tissue or components or additives which jeopardize the intended purpose to be achieved with the present invention, especially in the sintered ceramic.

Thus, for examples components or additives added in an amount which finally (e.g. after a sintering step) results in a non-tooth-coloured article are usually not contained in the final dental restoration. Typically, an article is characterized as tooth coloured if it can be allocated a colour from the Vita™ colour code system, known to the person skilled in the art.

Moreover, if possible, the composition should not or only contain a small amount of ingredients which can be detrimental to the firing equipment during the sintering process. According to a specific embodiment, the liquid composition does not contain reactive organic monomers (i.e. chemically reactive moieties like double bonds, e.g. (meth)acrylates). Thus, after preparation, the liquid composition does not exhibit chemical reactivity under ambient conditions, i.e. components being present in the composition do not react with each other at ambient conditions.

The liquid composition does also typically not contain initiators suitable to start the curing reaction of reactive monomers.

The liquid composition does typically also not contain filler or filler particles. Thus, particles which can be removed by filtration and/or precipitate from the composition are not contained. According to one embodiment, the liquid composition does not comprise nano-sized particles.

Nano-sized particles typically have a (hydrodynamic) diameter in the range from 1 nm to 500 nm or from 2 nm to 100 nm or from 3 nm to 20 nm. The diameter should be tailored to be compatible with (i.e. being smaller than) the pore size of the ceramic material to which the composition should be applied. If desired, the (hydrodynamic) diameter of the particles can be determined by a dynamic light scattering method.

Dynamic Light Scattering (DLS) is an analytical method using the Brownian motion of particles in a solvent to determine their size. Basis of the method is that smaller particles move faster than bigger particles. A laser is used to irradiate a sample and the light scattered by the particles is detected. Small, fast moving particles cause quick fluctuations of the detected signal, while bigger and slower particles cause slower fluctuations.

The DLS method determines the so called "hydrodynamic diameter" of the dispersed particles. The moving particles possess a shell of solvent that moves along with them through the solution. The hydrodynamic diameter is the diameter of the solid particle plus the solvent shell. As a result, the actual particle is always smaller than the measured diameter. A device which can be used for the DLS measurements is the Zetasizer™ Nano ZS (Malvern). Nano-sized particles which are typically not contained are $ZrO_2$ or $TiO_2$ particles.

The dental zirconia article does usually not contain glass, glass ceramic materials, lithium disilicate ceramic materials, or combinations thereof. Further, the producing of the dental zirconia article described in the present text does typically also not require the application of a hot isostatic pressing step (HIP).

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

Measurements
Method for Measuring N2 Sorption Isotherms, BET Surface Area, Pore Volume, Average Connected Pore Diameter The samples were run on either on a QUANTACHROME AUTOSORB-1 BET Analyzer" (Quantachrome Instruments, Boynton Beach, Fla.) or a BELSORP-mini instrument (BEL Japan Inc., Osaka, Japan). The samples were weighed and outgassed at 200° C. for two days then subjected to a $N_2$ sorption process with an appropriate number and distribution of measurement points, e.g. 55 adsorb points and 20 desorb points from a $p/p_0$ range $1\times10^{-6}$ to 1 and back to 0.05 giving full isotherms. The specific surface area S was calculated by the BET method (Details regarding calculation see Autosorb-1 Operating Manual Ver. 1.51 IV. Theory and Discussion; Quantachrome Instruments, Inc.). The total pore volume $V_{liq}$ is derived from the amount of vapor adsorbed at a relative pressure close to unity ($p/p_0$ closest to 1), by assuming that the pores are then filled with liquid adsorbate (Details regarding calculation see Autosorb-1 Operating Manual Ver. 1.51 IV. Theory and Discussion; Quantachrome Instruments, Inc.). The average pore diameter (d) is calculated from the surface area (S) and the total pore volume ($V_{liq}$):

$$d = \frac{4 V liq}{S}.$$

Average Grain Size

If desired, the average grain size can be determined with the Line Intercept Analysis. FESEM micrographs with 70,000 times magnification are used for grain size measurement. Three or four micrographs taken from different areas of the sintered body are used for each sample. Ten horizontal lines, which are spaced at roughly equal intervals across the height of each micrograph, are drawn. The numbers of grain boundary intercepts observed on each line are counted and used to calculate the average distance between intercepts. The average distance for each line is multiplied by 1.56 to determine the grain size and this value is averaged over all the lines for all micrographs of each sample.

Particle Size

If desired, particle size measurements can be done using a light scattering particle sizer equipped with a red laser having a 633 nm wavelength of light (obtainable under the trade designation "ZETA SIZER—Nano Series, Model ZEN3600" from Malvern Instruments Inc., Westborough, Mass.). Each sample is analyzed in a polystyrene sample cuvette. The sample cuvette is filled with a particle dispersion containing 1 wt.-% solids. The sample cuvette is then placed in the instrument and equilibrated at 25° C. The automatic size-measurement procedure can then be run. The instrument automatically adjusts the laser-beam position and attenuator setting to obtain the best measurement of particle size.

The method of Photon Correlation Spectroscopy (PCS) is used by the software to calculate the particle size. PCS uses the fluctuating light intensity to measure Brownian motion of the particles in the liquid.

Density

If desired, the density of the pre-sintered or sintered material can be measured by an Archimedes technique. The measurements is made on a precision balance (identified as "AE 160" from Mettler Instrument Corp., Hightstown, N.J.) using a density determination kit (identified as "ME 33360" from Mettler Instrument Corp.).

To measure the density of the pre-sintered material the sample is first weighed in air (A). Then the sample is immersed in water using vacuum overnight. The immersed sample is weighed in air (B) and then weighed under water (C). The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho = (A/(B-C))\, \rho0$, where $\rho 0$ is the density of water.

To measure the density of the sintered material the sample is first weighed in air (A), then immersed in water (B) The water is distilled and deionized. One drop of a wetting agent (obtained under trade designation "TERGITOL-TMN-6" from Dow Chemical Co., Danbury, Conn.) is added to 250 ml of water. The density is calculated using the formula $\rho = (A/(A-B))\, \rho0$, where $\rho0$ is the density of water.

The relative density can be calculated by reference to the theoretical density ($\rho t$) of the material, $\rho rel = (\rho/\rho t)100$.

Vickers Hardness

If desired, the Vickers hardness can be determined according to ISO 843-4 with the following modifications: The surface of the samples are ground using silicon carbide grinding paper (P400 and P1200). The test forces are adjusted to the hardness level of samples. Used test forces were between 0.2 kg and 2 kg and were applied for 15 s each indentation. A minimum of 10 indentations is measured to determine the average Vickers hardness. The tests can be conducted with a hardness tester Leco M-400-G (Leco Instrumente GmbH).

Biaxial Flexural Strength

If desired, the biaxial flexural strength can be determined according to ISO 6872 (2008) with the following modifications: The sample is sawn into wafers with a thickness of 1 to 2 mm using a dry or wet cut saw The diameter of the samples should be between 12 and 20 mm. Each wafer is centred on a support of three steel balls. The support diameter depends on the sample diameter and should have maximum 14 mm and should be at least 1 mm smaller than the sample diameter. The punch diameter in contact with the wafer is 3.6 mm. The punch is pushed onto the wafer at a rate of 0.1 mm per min. A minimum of 6 samples is measured to determine the average strength. The tests can be conducted in an Instron 5566 universal testing machine (Instron Deutschland GmbH).

Materials Used

Zirconia Sample A

A sol composition containing Zr oxide (91.1 wt.-%; calculated as $ZrO_2$), Hf oxide (1.8 wt.-%; calculated as $HfO_2$) and Y oxide calculated as $Y_2O_3$ (7.1 wt.-%) was prepared with a hot tube reactor by using the respective metal acetates. The sol was concentrated and water was partially replaced by a TFF process. The concentrated sol was gelled by mixing the sol, an acrylic monomer, ethanol, and a radical polymerization initiator. The gel was filled into a mold and cured. The cured gel was removed from the mold and immersed in pure ethanol to exchange water with ethanol in the gel. The gel was then supercritically extracted with $CO_2$. After that the gel was de-bindered and pre-sintered at 1020° C. A more detailed description of the process can be found e.g. in WO 2013/055432 (3M). The obtained sample was sliced into discs (diameter: 17 mm; thickness: 1.5 mm).

Zirconia Sample B

Bindered $ZrO_2$ powder (TZP) was pressed into cylindric blocks by applying a pressure of 200 MPa. The blocks were de-bindered and pre-sintered at 900° C. The obtained samples were sliced into discs (diameter: 17 mm; thickness: 1.5 mm).

Liquid Compositions and Process of Application

All compositions are calculated to contain the same mass percentage of whitening agent (0.425 g agent on 5 g composition).

Inventive Example 1 (IE1)

0.500 g of phosphoric acid (85%) is mixed with 4.500 g of glycerol by stirring until a homogeneous solution is obtained. The mixture was applied with a microbrush to a dry disc of porous pre-sintered (1020° C.) Zirconia Sample A. Half of the disc is painted with the liquid. After that, the material was put into a furnace and sintered at 1300° C. for 2 hours. As a result, dense zirconia disc with one white, opaque half was obtained (see FIG. 1).

Inventive Example 2 (IE2)

0.500 g of phosphoric acid (85%) was mixed with 4.500 g of deionized water by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with one white, opaque half was obtained (see FIG. 1).

Comparative Example 1 (CE1)

0.654 g of nitric acid (65%) was mixed with 4.346 g of de-ionized water by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 2 (CE2)

0.434 g of sulfuric acid (98%) was mixed with 4.566 g of glycerol by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 3 (CE3)

0.434 g of sulfuric acid (98%) was mixed with 4.566 g of deionized water by stirring until a homogeneous solution is obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 4 (CE4)

1.700 g of hydrochloric acid (25%) was mixed with 3.300 g of glycerol by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 5 (CE5)

1.700 g of hydrochloric acid (25%) was mixed with 3.300 g of deionized water by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 6 (CE6)

0.425 g of acetic acid (100%) was mixed with 4.575 g of glycerol by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Comparative Example 7 (CE7)

0.425 g of acetic acid (100%) was mixed with 4.575 g of deionized water by stirring until a homogeneous solution was obtained. The mixture was applied with a microbrush to a dry disc of porous pre-sintered (1020° C.) Zirconia Sample A. Half of the disc was painted with the liquid. After that, the material was put into a furnace and sintered at 1300° C. for 2 hours. As a result, dense zirconia disc with no white, opaque region was obtained (see FIG. 1).

Figure 1:
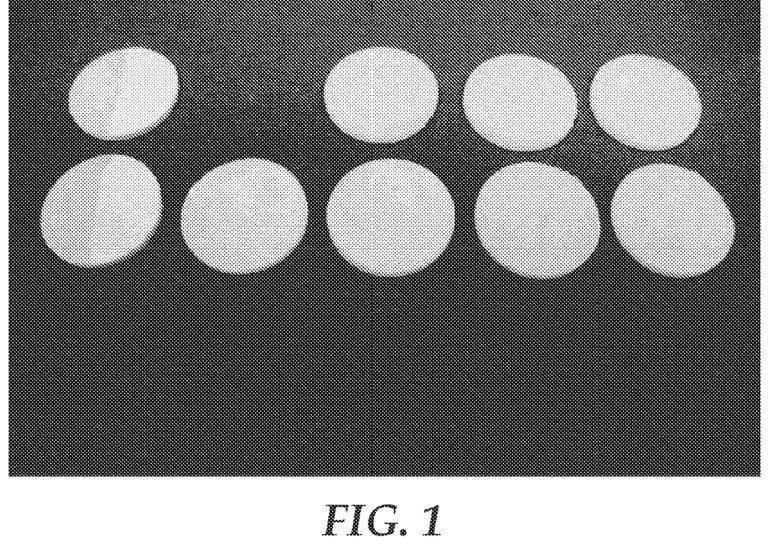
FIG. 1 shows sintered zirconia discs to which liquid compositions described in the present text have been applied.

In FIG. 1 the results obtained for the Zirconia Samples A are shown:

From left to right: samples obtained by using the following agents: phosphoric acid (Inventive Example), nitric acid, sulfuric acid, hydrochloric acid and acetic acid (Comparative Examples)

Upper row: solvent: glycerol;

Lower row: solvent: water;

The results obtained for the Zirconia Samples A are also given in the table below.

|  | IE1 | IE2 | CE1 | CE2 | CE3 | CE14 | CE5 | CE6 | CE7 |
|---|---|---|---|---|---|---|---|---|---|
| Opacifying intensity | strong | strong | none | none | none | none | none | none | none |
| Sharpness/definition | sharp | sharp | — | — | — | — | — | — | — |

Result: Only the phosphorus containing samples showed an opacifying effect that was well defined and appeared only where the inventive composition was applied.

Inventive Example 3 (IE3)

0.500 g of phosphoric acid (85%) was mixed with 4.500 g of de-ionized water by stirring until a homogeneous solution was obtained. The mixture was applied with a microbrush to a dry disc of porous pre-sintered Zirconia Sample B. Half of the disc was painted with the liquid. After that, the material was put into a furnace and sintered at 1450° C. for 2 hours. As a result, dense zirconia disc with one white, opaque half was obtained, the opacifying effect being intense and well defined.

Inventive Example 4 (IE4)

0.433 g of phosphoric acid, diammonium salt (98%) was mixed with 4.566 g of de-ionized water by stirring until a homogeneous solution was obtained. The mixture was applied with a microbrush to a dry disc of porous pre-sintered Zirconia Sample B. Half of the disc was painted with the liquid. After that, the material was put into a furnace and sintered at 1450° C. for 2 hours. As a result, dense zirconia disc with one white, opaque half was obtained, the opacifying effect being intense and well defined.

Comparative Example 8 (CE8)

0.433 g of triethyl phosphate (98%) was mixed with 4.566 g of de-ionized water by stirring until a homogeneous solution was obtained. The mixture was applied with a microbrush to a dry disc of porous pre-sintered Zirconia Sample B. Half of the disc was painted with the liquid. After that, the material was put into a furnace and sintered at 1450° C. for 2 hours. As a result, dense zirconia disc with one white, opaque half was obtained, the opacifying effect being weak and blurry, because the whitening agent had spread through the zirconia material.

The results obtained for the Zirconia Samples B are described in the table below.

|  | IE3 | IE4 | CE8 |
|---|---|---|---|
| Opacifying intensity | strong | strong | medium |
| Sharpness/definition | sharp | sharp | blurry |

All agents led to an opacifying effect on the treated samples. However, only the agents with functional groups that could interact with the zirconia surface of the samples led to a well defined opacifying effect that appeared only where the inventive composition was applied.

The invention claimed is:

1. A process for selectively treating parts of the surface of a porous dental zirconia article, the process comprising:
    a) providing a liquid composition and a porous 3-dimensional dental zirconia article having an outer and inner surface,
    b) applying the liquid composition to only a part of the outer surface and/or inner surface of the porous dental zirconia article,
    the liquid composition comprising:
    a whitening agent comprising a phosphorus containing component,
    the phosphorus containing component comprising a phosphate, phosphone or phosphine moiety,
        wherein at least one P—O unit of the phosphate, phosphone or phosphine moiety is dissociable or able to interact with zirconia.

2. The process of claim 1, the phosphorus containing component being selected from acids comprising phosphate, phosphone or phosphine moieties, salts comprising phosphate, phosphone or phosphine moieties or mixtures of acids and salts thereof.

3. The process of claim 1, the phosphorus containing component being characterized by formula (1):

(R1O)(R2)(R3)P=X(1)

with X being O or S,
R1 being H, ammonium, a metal ion or an organic moiety,
R2 and R3 being independently selected from R1 or OR1,
with the proviso that at least one R1, R2 or R3 is able to dissociate from O in the liquid composition or comprises an oxygen-containing functional group which can interact with zirconia.

4. The process of claim 1, the liquid composition being characterized by at least one of the following features:
    viscosity: from 10 mPa*s to 10,000 at 23° C.,
    being transparent to visible light.

5. The process of claim 1, the liquid composition comprising the whitening agent in an amount of 5 to 60 wt.-% with respect to the whole composition.

6. The process of claim 1, the liquid composition comprising in addition one or more of the following components:
    a solvent being able to dissolve the whitening agent, preferably selected from water, alcohols, ketons and mixtures thereof;
    additives;
    and mixtures thereof.

7. The process of claim 1, the liquid composition being essentially free of one, more or all of the following components:
    insoluble components,
    nano-sized particles having a diameter from 1 nm to 500 nm,
    colouring ions selected from iron, erbium, praseodymium or mixtures thereof, reactive organic monomers, initiators suitable for curing reactive organic monomers, and combinations thereof.

8. The process of claim 1, the liquid composition being contained in a pen, the pen comprising a housing, a brush tip, a removable cap and a reservoir for storing the liquid composition described in claim 1.

9. The process of claim 1, the porous dental zirconia article being characterized by either of the following features:

the porous dental zirconia article not showing a N2 adsorption and/or desorption of isotherm type IV according to IUPAC classification and having a BET surface from 2 to 20 m$^2$/g;

the porous dental zirconia article showing a N2 adsorption and/or desorption of isotherm type IV according to IUPAC classification and having a BET surface from 10 to 200 m$^2$/g.

10. The process of claim 1, the porous dental zirconia article being obtained by either of the following processes:

a process comprising the steps of pressing zirconia powder to a 3-dimensional object and partially sintering the 3-dimensional object, or a process comprising the step of heat-treating a zirconia aerogel.

11. The process of claim 1, the porous dental zirconia article being characterized by at least one, more or all of the following features:

showing a nitrogen adsorption and desorption isotherm with hysteresis loop;

showing a hysteresis loop of type H1 according to IUPAC classification;

showing a N2 adsorption and desorption isotherm with a hysteresis loop in a p/p$_0$ range of 0.70 to 0.95;

average connected pore diameter: from 10 to 100 nm;

average grain size: less than 100 nm;

BET surface: from 10 to 200 m$^2$/g;

biaxial flexural strength: from 10 to 40 MPa;

Vickers hardness: from 25 to 150;

density: 30 to 95% of theoretical density;

x, y, z dimension: at least 5 mm;

having an isotropic shrinkage behaviour.

12. The process of claim 1, comprising:

drying the porous dental zirconia article, the surface of which has been selectively treated with the liquid composition of claim 1, sintering the porous dental zirconia article.

* * * * *